United States Patent [19]

Pein et al.

[11] Patent Number: 5,077,301
[45] Date of Patent: Dec. 31, 1991

[54] 4-(HYDROXYDIPHENYLMETHYL)-1-PIPERIDYLPHENYLALKANE DERIVATIVES AS ANTIHISTAMINES AND METHODS OF TREATMENT OF AN ALLERGIC RESPONSE

[75] Inventors: Eckhardt Pein, Northeim; Helmut Ritter, Wuppertal; Reinhard Laven, Salzgitter, all of Fed. Rep. of Germany

[73] Assignee: Schaper & Bruemmer GmbH & Co. KG, Salzgitter, Fed. Rep. of Germany

[21] Appl. No.: 528,966

[22] Filed: May 25, 1990

[30] Foreign Application Priority Data

May 26, 1989 [DE] Fed. Rep. of Germany ....... 3917241

[51] Int. Cl.$^5$ ........................................ A61K 31/445
[52] U.S. Cl. .................................................. 514/317
[58] Field of Search ......................................... 514/317

[56] References Cited

U.S. PATENT DOCUMENTS 3,014,037 12/1961 Rorig ............................. 260/294.7
3,068,237 12/1962 Rorig ............................. 260/294.7

FOREIGN PATENT DOCUMENTS 23033058 8/1973 Fed. Rep. of Germany .
23033069 8/1973 Fed. Rep. of Germany .
25033629 8/1975 Fed. Rep. of Germany .
25067703 9/1975 Fed. Rep. of Germany .
30074987 10/1980 Fed. Rep. of Germany .

OTHER PUBLICATIONS

Hiroshi Ohtaka et al., "Benzylpiperazine Derivatives VII, Studies on the Role of the Nitrogen Atom in the Cerebral Vasodilating Activity of 1-Benzyl-4-Diphenylmethylpiperazine Derivatives", Chem. Pharm. Bull., 35, 1987, pp. 4637–4641.

Primary Examiner—Leonard Schenkman
Attorney, Agent, or Firm—Foley & Lardner

[57] ABSTRACT

4-(Hydroxydiphenylmethyl)-1-piperidylphenylalkane derivatives as antihistamines of the formula

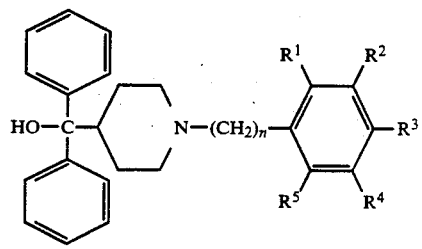

and pharmaceutically acceptable salts of such derivatives are disclosed
in which
n is an integer between 0 and 2,
$R^1$–$R^5$ represent, independently of one another, hydrogen and at least one of them represents a linear or branched alkyl radical with 1–4 carbon atoms, a $C_1$–$C_3$-alkoxy radical or a hydroxyl radical. A method of treatment of allergic response in mammals is also disclosed.

10 Claims, 1 Drawing Sheet

FIG. I
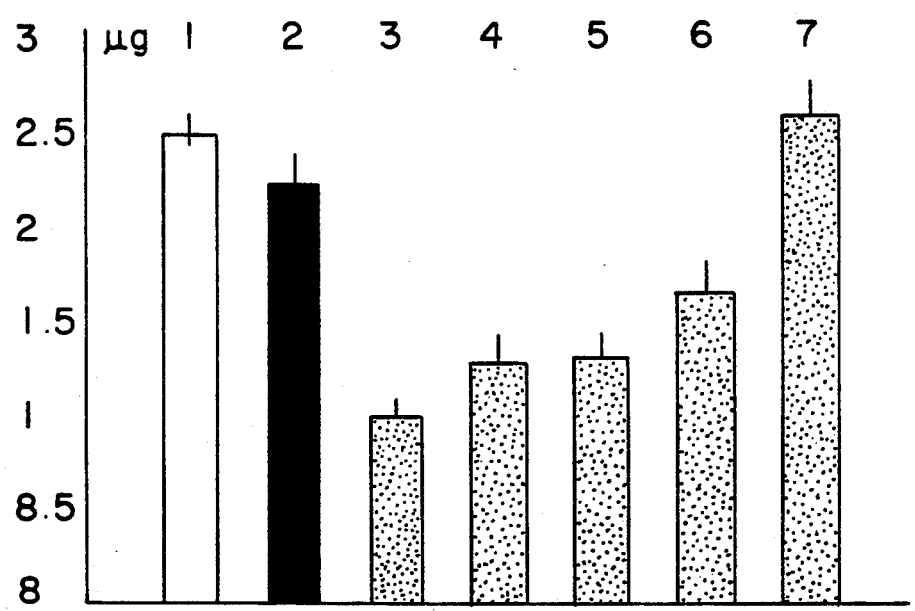

4-(HYDROXYDIPHENYLMETHYL)-1-PIPERIDYLPHENYLALKANE DERIVATIVES AS ANTIHISTAMINES AND METHODS OF TREATMENT OF AN ALLERGIC RESPONSE

BACKGROUND OF THE INVENTION

The present invention relates to 4-(hydroxydiphenylmethyl)-1-piperidylphenylalkane derivatives and their use as antihistamines.

It is known that 4-diphenylmethylpiperidine derivatives can be used as antihistamines. A corresponding action has been described for piperidinobutanols and 1-piperidinopropanols in DE 2,506,770, DE 2,303,305, DE 2,303,306, DE 2,503,362 and DE 3,007,498.

α-[4-(1,1-Dimethylethyl)phenyl]-4-(hydroxydiphenylmethyl)-1-piperidinobutanol, INN terfenadine, is used in therapy as an antihistamine.

Many substances based on α,α-diphenyl-4-piperidylmethanol, including some with pharmaceutical activity, have been described. U.S. Pat. No. 3,014,037 and U.S. Pat. No. 3,068,237 describe these substances as papaverine-type spasmolytics with musculotropic activity, and as substances having antisecretory activity. It has also been reported that the barbiturate sleeping time of mammals is prolonged.

It has been reported that α,α-diphenyl-4-piperidylmethanol derivatives and compounds that are closely chemically related display a cerebral vasodilating action, i.e., musculotropic spasmolytic action can be detected in this vascular region. *Chem. Pharm. Bull.* 35, 4637-4641 (1987).

SUMMARY OF THE INVENTION

It is an object of the present invention to provide an antihistamine capable of counteracting an allergic response in mammals.

It is a further object of the invention to provide an antihistamine capable of counteracting an allergic response in mammals that can be administered in a considerably lower individual dose and with fewer side effects as compared to piperidino alcohol derivatives of the terfenadine type.

It is another object of the invention to provide a method of treatment of allergic disorders in mammals.

These and other objects of the invention are provided by an antihistamine comprising a 4-(hydroxydiphenylmethyl)-1-piperidylphenylalkane derivative of the formula

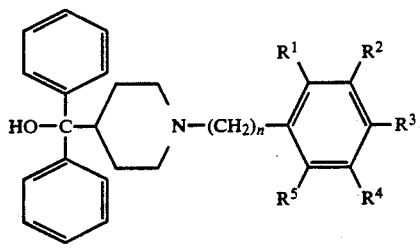

or a pharmaceutically-tolerated salt thereof,
in which
n is an integer between 1 and 2,
$R^1$-$R^5$ represent, independently of one another, hydrogen and at least one radical selected from the group consisting of a linear or branched alkyl radical having 1-4 carbon atoms, a $C_1$-$C_3$-alkoxy radical and a hydroxyl radical and a pharmaceutically-acceptable excipient.

The objects of the invention are also provided by a method of treatment of an allergic response in a mammal, comprising the step of administering to the mammal an antihistamine comprising the 4-(hydroxydiphenylmethyl)-1-piperidylphenylalkane derivative, or a pharmaceutically-tolerated salt thereof, in an amount effective to counteract the allergic response.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWING

FIG. 1 is a bar graph summarizing data which demonstrate the relative antihistamine action of compounds within the present invention versus the piperidino alcohol derivative terfenadine. Shown are values of dyestuff content in areas of mouse dorsal skin after intradermal injection of 1 μg of histamine, which in turn followed treatment with:

1. physiological saline,
2. 3 mg/kg terfenadine,
3. 3 mg/kg 4-(hydroxydiphenylmethyl)-1-piperidyl-(3-methylphenyl)methane HCl,
4. 3 mg/kg (4-hydroxydiphenylmethyl)-1-piperidyl-4-(methoxyphenyl)ethane HCl,
5. 3 mg/kg 4-(hydroxydiphenylmethyl)-1-piperidyl-(3-methoxyphenyl)ethane HCl, and
6. 3 mg/kg 4-(hydroxydiphenylmethyl)-1-piperidyl-(4-tert-butyl-phenyl)methane HCl
7. 6 mg/kg 4-(hydroxydiphenylmethyl)-1-piperidylmethane.

DESCRIPTION OF THE PREFERRED EMBODIMENTS 4-(Hydroxydiphenylmethyl)-1-piperidylphenylalkane derivatives can be used according to the invention as effective antihistamines when, in the general structural formula hereinafter,

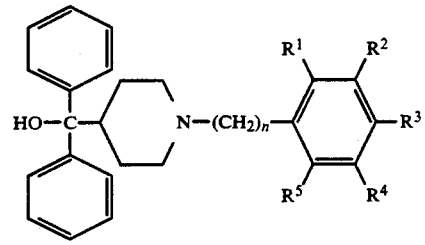

n is 1 or 2, and
$R^1$-$R^5$ represent, independently of one another, hydrogen and at least one selected from the group consisting of a linear or branched alkyl radical having 1-4 carbon atoms, a $C_1$-$C_3$- alkoxy radical and a hydroxyl radical.

Particularly suitable radicals are methoxy groups or $C_1$-$C_4$-alkyl groups. Preferably the phenyl ring has one or two of these groups.

The 4-(hydroxydiphenylmethyl)-1-piperidylphenylalkane derivatives possess surprising and unexpected pharmacological action. Illustrative of the mode of action of the described group of substances is the action of [4-(hydroxydiphenylmethyl)-1-piperidyl]-(3-methoxyphenyl)methane.

Experiments were carried out on the isolated ileum and on the isolated trachea of guinea pigs in a typical manner in vitro in a suitable organ bath. Histamine dihydrochloride was used as a spasmogen in a final concentration of 0.2-2 µg/ml, depending on the organ preparation. The activity of the compounds was determined from the reactive spasmolysis, i.e., the relative decrease in the force of contractions compared with zero dose. The concentration-action relation was calculated from the non-linear regression between dose and action from at least six individual tests.

The $ED_{50}$ on guinea pig ileum was 62 ng/ml for terfenadine and 29 ng/ml for the [4-(hydroxydiphenylmethyl)-1-piperidyl]-(3-methoxyphenyl)methane compound. The $ED_{50}$ on the isolated tracheal preparation was 4.1 µg/ml for terfenadine and 3.5 µg/ml for the [4-(hydroxydiphenylmethyl)-1-piperidyl]-(3-methoxyphenyl)methane compound.

The potencies of all the 4-(hydroxydiphenylmethyl)-1-piperidylphenylalkane derivatives described were comparable. Overall, the derivatives exceeded the action of terfenadine.

Considerable differences in action emerged, unexpectedly and surprisingly, from the in vivo testing of the 4-(hydroxydiphenylmethyl)-1-piperidylphenylalkane derivatives on mice after oral administration.

The experiments were carried out on male NMRI mice with a body weight of 25-30 g. The capillary permeability is artificially increased by o intradermal injection of 1 µg of histamine, thus allowing the release of an intravenously-injected dyestuff. The dyestuff concentration determined by photometry in a defined area of skin can be designated a measure of the antihistamine activity.

FIG. 1 represents the influence on the capillary damage generated by intradermal injection of 1 µg of histamine on the mouse dorsal skin. These results again showed the superior antihistamine action of the 4-(hydroxydiphenylmethyl)-1-piperidylphenylalkane derivatives as compared to terfenadine.

Elucidation of the profile of pharmacological action of the α,α-diphenylpiperidylphenylalkane derivatives revealed that the antihistamine action for the substances described was greater by a factor of 2-3 than the musculotropic spasmolytic action, i.e., the antihistamine action represents the predominant pharmacodynamic property of the claimed α,α-diphenylpiperidylphenylalkane derivatives.

The newly-discovered and unexpected action of the described class of substances means that a considerably lower individual dose and fewer undesired effects are expected during therapy of allergic disorders, as compared to the piperidino alcohol derivatives of the terfenadine type.

The pronounced affinity of the 4-(hydroxydiphenylmethyl)-1-piperidylphenyl alkane derivatives for the $H_1$-histamine receptors of the skin leads to the expectation that there will also be therapeutic efficacy even at concentrations where corresponding piperidino alcohol derivatives do not display an adequate action.

The 4-(hydroxydiphenylmethyl)-1-piperidylphenylalkane derivatives described can be administered in pure form or in customary pharmaceutical formulations orally, parenterally or rectally, and administered in aerosol or powdered form.

The range of uses of the 4-(hydroxydiphenylmethyl)-1-piperidylphenylalkane derivatives described as antihistamines extends both to the human and to the entire veterinary medical sector.

The in vivo activity decreased distinctly with increasing number of carbon atoms for n and approached the weaker level of action of terfenadine at $n=3$.

Investigation of the duration of action of the 4-(hydroxydiphenylmethyl)-1-piperidylphenylalkane derivatives revealed, additionally and unexpectedly, that the substances according to the invention possessed, after a single oral dose of 6 mg/kg of body weight for up to more than 6 hours, a distinct inhibition of the histamine-induced skin weal in the mouse. By contrast, after 4 hours it was no longer possible to measure reliably an antihistamine action after oral administration of a comparable dose of the comparison substance terfenadine.

The experimental results demonstrate that the 4-(hydroxydiphenylmethyl)-1-piperidylphenylalkane derivatives described represent effective antihistamines, antiallergics and bronchodilators which lead to the expectation of effective treatment of corresponding pathological states.

The invention embraces pharmaceutically-acceptable salts of the 4-(hydroxydiphenylmethyl)-1-piperidylphenylalkane derivatives. Pharmaceutically-acceptable acid addition salts are those with suitable organic and inorganic acids such as hydrochloric acid, sulfuric acid, phosphoric acid or carboxylic acids and dicarboxylic acids. Suitable organic acids include acetic acid, fatty acids such as stearic acid, lauric acid, oleic acid or palmitic acid, glycolic acid, lactic acid, pyruvic acid, malonic acid, succinic acid, fumaric acid, malic acid, tartaric acid, citric acid, cyclamic acid, ascorbic acid, benzoic acid, 4-hydroxybenzoic acid, cinnamic acid, salicylic acid, mandelic acid and the suitable sulfonic acids such as methanesulfonic acid, ethanesulfonic acid and β-hydroxyethanesulfonic acid. The salts are formed in a conventional manner.

Examples of compounds according to the invention include:

1. [4-(Hydroxydiphenylmethyl)-1-piperidyl]-(3-methoxyphenyl)methane,
2. [4-(hydroxydiphenylmethyl)-1-piperidyl]-(3-methoxyphenyl)ethane,
3. 1-[4-(Hydroxydiphenylmethyl)-1-piperidyl]-2-(3-methoxyphenyl)ethane, and
4. 4-(hydroxydiphenylmethyl)-1-piperidyl-(4-tert.-butylphenyl)methane.

The derivatives of the 4-(hydroxydiphenylmethyl)-1-piperidylphenylalkanes according to the invention can be administered orally, parenterally, e.g., intravenously, subcutaneously, intramuscularly, intranasally or rectally, and administered in aerosol or powdered form.

The dose of the administered substance depends on the nature of the use and the individual sensitivity of the person to be treated. The dose range extends from 0.1-10 mg/kg of body weight/day to achieve the desired effect.

The substances according to the invention can be prepared in a variety of ways. By way of illustration, four exemplary products are prepared according to the synthesis examples which follow:

1. Synthesis of 1-[4-(hydroxydiphenylmethyl)-1-piperidyl]-2-(4-methoxyphenyl)ethane A mixture of 4 g of α,α-diphenyl-4-piperidinomethanol, 0.94 g of powdered potassium hydroxide and 200 mg of KI are dispersed in 50 ml of toluene in a 250 ml round-bottomed flask. Addition of 2.3 ml of 4-methoxyphenylethyl chloride is followed by heating under reflux for 3 days.

After cooling to room temperature, turbidity is removed by filtration, the solvent is distilled off, the residue is dissolved in 50 ml of chloroform, and the solution is extracted by shaking with water several times. The organic phase is subsequently dried with $MgSO_4$, the solvent is distilled off, and ether is poured onto the residue, resulting in a white crystalline product.

For further purification, the crude product is dissolved in methylene chloride/ethyl acetate (1:1), and slight impurities are removed using a column packed with silica gel (run height 4 cm).

Removal of the solvent by distillation results in a colorless crystalline product. Melting point: 120°. Characteristic IR bands: 1608, 1505, 1440, 1240, 705 $cm^{-1}$.

2. Synthesis of 4-(Hydroxydiphenylmethyl)-1-piperidyl-(3-methoxyphenyl) methane hydrochloride A mixture of 8.0 g (30 mmol) of α,α-diphenyl-4-piperidinomethanol, 2.35 g (15 mmol) of 3-methoxybenzyl chloride, 0.5 g of triethylamine and 30 ml of THF is stirred under reflux for 1 hour, during which a colorless precipitate separates out. After cooling to 20° C., the precipitate is filtered off, and the filtrate is concentrated. For working up, the residue is taken up in 5 ml of methylene chloride, and ethereal HCl solution is added until no further precipitation occurs. The mixture is diluted with 30 ml of methylene chloride, the precipitate is filtered, and the filtrate is concentrated. Drying of the oily residue at 40° C. in vacuo results in 6.5 g of final product. Decomposition point about 80° C. Characteristic IR bands: 3360, 1590, 1480, 1438, 1256, 690 cm.

3. Synthesis of 1-[4-(Hydroxydiphenylmethyl)-1-piperidyl]-2-(3-methoxyphenyl)ethane 3-Methoxyacetyl chloride (2.0 g 10.B mmol) is added dropwise, at 0° C. under nitrogen, to a stirred mixture of 5.78 g (21.7 mmol) of α,α-diphenyl-4-piperidinomethanol and 2.2 g of triethylamine in 20 ml of absolute THF. After the mixture has been stirred at room temperature for 4 hours it is taken up in 20 ml of chloroform, the precipitate is filtered, and the filtrate is evaporated to dryness. The residue is dissolved in the minimum amount of methylene chloride/ethyl acetate (1:1, vol.) and purified on a column packed with silica gel (height 7 cm, diameter 3 cm) with ethyl acetate as mobile phase. Concentration and drying result in 2.5 g of product which reveals a characteristic amide band at 1630 cm. in the IR spectrum.

$LiAlH_4$ (0.25 g) and then 2.5 g of the product from the first stage are added to 20 ml of THF which has been dried over LiAlH . Further doses of $LiAlH_4$, each of about 100 mg, are added at intervals of 30 minutes while stirring at room temperature for 2 hours. This is followed by heating under reflux for one hour. After cooling, the $LiAlH_4$ is cautiously decomposed with a little water, and $Al_2O_3$ is added to the mixture until a clear supernatant solution results. Filtration and removal of the solvent by distillation are followed by addition of ethereal HCl solution to the oily residue until no further precipitate results. After addition of 50 ml of ether, the final product is filtered off and dried. The yield is 1.7 g of a colorless product. Melting point: >80° C. (decomposition). Characteristic IR signals: 3370 (OH), 1595 (aromatic), 1255, 1150, 745 and 695 $cm^{-1}$:

4. Synthesis of 4-(hydroxydiphenylmethyl)-1-piperidyl-(4-tert.-butylphenyl)methane 4-Tert.-butylbenzyl bromide (2.4 ml), 7 g of α,α-diphenyl-4-piperidinomethanol and 1.9 ml of triethylamine are dissolved in 90 ml of absolute THF and heated under reflux for hour. This is followed by filtration and concentration of the filtrate to an oily consistency. It is subsequently taken up in 50 ml of ether, an equal amount of petroleum ether is added, and filtration is carried out after cooling. The oil after evaporation is mixed with a little ether, and ethereal HCl solution is added to the solution to form the hydrochloride. Yield: 3.5 g, melting point: 110° C. (decomposition). Characteristic IR data: 3300 (OH), 2960 (CH), 1615/1600 (aromatic), 1450, 750 and 710 $cm^{-1}$ (KBr).

What is claimed is:

1. A method of treatment of an allergic response in a mammal comprising the step of administering to the mammal an antihistamine comprising a 4-(hydroxydiphenylmethyl)-1-piperidylphenylalkane derivative of the formula

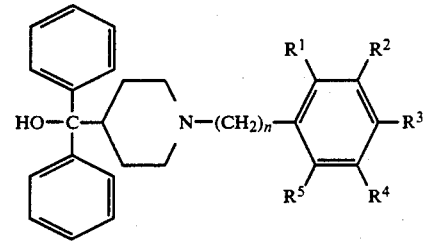

and pharmaceutically-tolerated salts thereof, in which
n is an integer between 1 and 2,
$R^1$–$R^5$ represent, independently of one another, hydrogen and at least one radical selected from the group consisting of a linear or branched alkyl radical having 1–4 carbon atoms, a $C_1$–$C_3$-alkoxy radical and a hydroxyl radical; and
a pharmaceutically-acceptable excipient, in an amount effective to counteract the allergic response.

2. A method of treatment as claimed in claim 1, wherein the allergic response is an increase in capillary permeability in the skin and the antihistamine is administered in an amount effective to affect H1-histamine receptors in the skin to decrease capillary permeability.

3. A method of treatment as claimed in claim 2, wherein the amount of the derivative or its salt 0.1–10 mg/kg of body weight/day.

4. A method of treatment as claimed in claim 2, in which one or two of the radicals $R^1$–$R^5$ of the derivative represent a methoxy radical.

5. A method of treatment as claimed in claim 2, in which one or two of the radicals $R^1$–$R^5$ of the derivative represent a $C_1$–$C_4$-alkyl radical.

6. A method of treatment as claimed in claim 2, wherein n=1.

7. A method of treatment as claimed in claim 4, wherein n=1.

8. A method of treatment as claimed in claim 5, wherein n=1.

9. A method of treatment as claimed in claim 2, in which one of the radicals $R^1$–$R^5$ of the derivative represents a methoxy radical and another of the radicals $R^1$–$R^5$ represents a $C_1$–$C_4$-alkyl radical.

10. A method of treatment as claimed in claim 9, wherein n=1.

* * * * *